United States Patent [19]

Bommer et al.

[11] Patent Number: 5,004,811

[45] Date of Patent: Apr. 2, 1991

[54] TETRAPYRROLE AMINOCARBOXYLIC ACIDS

[75] Inventors: Jerry C. Bommer, Ogden; Bruce F. Burnham, Logan, both of Utah

[73] Assignee: Nippon Petrochemicals Company, Ltd., Tokyo, Japan

[21] Appl. No.: 137,750

[22] Filed: Dec. 24, 1987

[51] Int. Cl.$^5$ .............................................. C07B 47/00
[52] U.S. Cl. ..................................... 540/145; 540/460
[58] Field of Search ....................... 540/145, 410, 460

[56] References Cited

U.S. PATENT DOCUMENTS

| | | | |
|---|---|---|---|
| 4,649,151 | 3/1987 | Dougherty et al. | 540/145 |
| 4,656,186 | 4/1987 | Bommer et al. | 540/145 |
| 4,675,338 | 6/1987 | Bommer et al. | 540/145 |
| 4,693,885 | 9/1987 | Bommer et al. | 540/145 |

OTHER PUBLICATIONS

*Chemical Berischte*, 90, pp. 470–491, 1957, by Lautsch, et al.
*Hoppe-Sevler's Ztschr. Phy. Chem.*, 327, pp. 205–216, 1962, by Losse and Müller.
*Chimia*, 13, pp. 129–180, 1959, by Karrer.
*Tetrahedron Letters*, 23, pp. 2017–2020, 1978, by Pelter, et al.
*Current Microbiology*, 8, pp. 195–199, 1983, by Gauthier, et al.
*Zhurnal Organichesoi Kiii Mii*, 15, pp. 828–835, 1979, by Bacunbee, et al.

*Primary Examiner*—Mary C. Lee
*Assistant Examiner*—Robert C. Whittenbaugh
*Attorney, Agent, or Firm*—Scully, Scott, Murphy & Presser

[57] ABSTRACT

A fluorescent mono-, di-, or tri- or tetramide between an amino acid of the formula

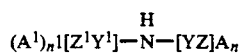

and a carboxy containing tetrapyrrole of the formula:

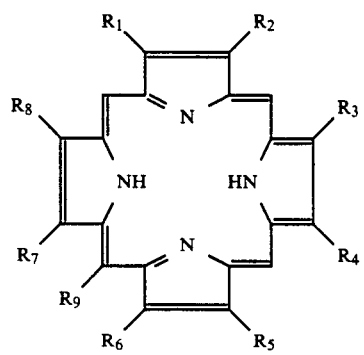

or the corresponding di or tetrahydrotetrapyrroles. The compounds herein are useful for the photodetection and phototreatment of tumors and/or cancerous tissues in animal hosts.

32 Claims, No Drawings

TETRAPYRROLE AMINOCARBOXYLIC ACIDS

FIELD OF THE INVENTION

This invention relates to new compounds which are useful in photodiagnosis and phototherapy, especially in the detection and treatment of tumors and cancerous tissues in the human or animal body.

DESCRIPTION OF THE PRIOR ART

It is known to irradiate tumors and cancerous tissues in the human body with intensive light following administration of a hematoporphyrin derivative in the wavelength range of 626 to 636 namometers to reduce and, at time, destroy the cancerous cells (see PCT published specification WO 83/00811). It is also known that porphyrins, especially the sodium salt of protoporphyrins, can maintain or promote the normal functions of cells and are useful for preventing the genesis, growth, metastasis, and relapse of malignant tumors. Japanese Published Patent Application No. 125737/76 describes the use of porphyrins as tumor inhibiting agents, exemplifying etioporphyrin, mesoporphyrin, protoporphyrin, deuteroporphyrin, hematoporphyrin, coproporphyrin, and uroporphyrin.

In Tetrahedron Letters No. 23, pp. 2017–2020 (1978), there is described an amino monocarboxylic acid adduct of the pigment bonellin obtained by extraction of principally the body wall of the marine echuroid *B. viridis*. The structure of these adducts is presumed to be an amide formed through either of the free carboxy groups of bonellin and the amino mono-carboxylic acid. Hydrolysis of the adduct yielded a mixture of valine, isoleucine, leucine and alloisoleucine. No use for these amino acid adducts is described in this reference.

That the tetrapyrroles cause intense photosensitivity in animals is well known and has been documented in numerous articles in literature, e.g., J. Intr. Sci. Vitaminol, 27, 521-527 (1981); Agric. Biol. Chem., 46(9), 2183-2193 (1982); Chem. Abst. 98, 276 (1983) and 88 6976m (1928).

SUMMARY OF THE INVENTION

The present invention is directed to novel fluroescent mono-, di-, tri-, or tetraamide of an amino acid and a carboxy containing tetrapyrrole compound of the formula:

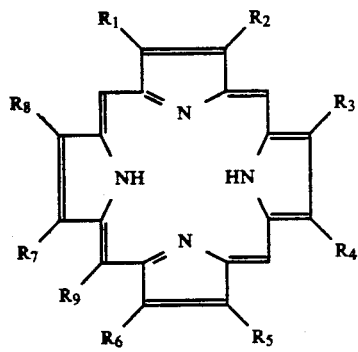

or the corresponding di- or tetrahydrotetrapyrroles, said amide linkage being formed between the amino group of the amino acid and a carboxy-containing substituent attached to the tetrapyrrole; wherien $R_1$ is methyl,

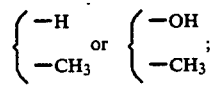

$R_2$ is H, vinyl, ethyl,

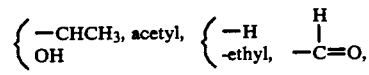

$CH_2CH_2CO_2H$, or $=CHCHO$;

$R_3$ is methyl,

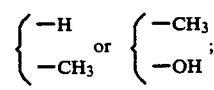

$R_4$ is H, vinyl, ethyl,

$CH_2CH_2CO_2H$, $=CHCHO$, or

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$ or

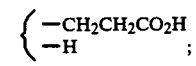

$R_8$ is methyl or

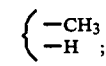

$R_9$ is H, COOH, $CH_2COOH$ or methyl; provided that when $R_1$, $R_2$, $R_3$, $R_4$, $R_7$ and $R_8$ represent . two substituents or are divalent and attached to the same carbon, the respective pyrrole ring to which attached is a dihydropyrrole;

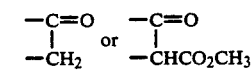

with the proviso that at least one of $R_1$-$R_9$ includes a free carboxyl group; and salts thereof; and wherein the amino acid has the formula:

wherein
each $A^1$ and A may be the same or different and are selected from the group consisting of COOH, $SO_3H$ or OH with the proviso that said compound contains at least one COOH or SO3H;

Z¹ and Z are independently an alkylene chain containing from 0–5 carbon atoms in the principal chain and up to a total of 8 carbon atoms;

Y¹ and Y are independently an alkylene chain containing from 0–5 carbon atoms in the principal chain and up to a total of 8 carbon atoms with the proviso that when both A and A¹ are other than S03H, then one of Y¹ or Y must contain at least one carbon atom in the principal chain; or Y¹ and Y taken together with the nitrogen to which they are attached form an N-heterocycle containing from 4–9 ring carbon atoms and up to a total of about carbon atoms; or Y¹ Z¹ or YZ individually may form a cycloalkyl group containing from 5 to 10 ring carbon atoms and up to a total of about 16 carbon atoms.

n¹ and n are independently 0, 1 or 2; and
n¹+n =2.

The compounds herein are useful for the photodiagnosis and phototreatment of tumors or cancerous tissue in an animal host.

DETAILED DESCRIPTION OF THE INVENTION

The products contemplated by this invention are cyclic and acyclic tetrapyrroles adducts indicated herein-above derived by various procedures from naturally-occuring tetrapyrroles. The cyclic tetrapyrroles have as their common parent tetrapyrrole, uroporphyrinogen, and possess the following ring structure:

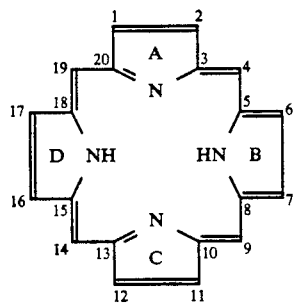

in which the positions in the molecule are numbered 1–20, and the rings identified by letters A, B, C and D, and also include perhydro-, e.g., dihydro- and tetrahydro-, derivatives of the said ring structure, e.g., compounds in which one or more double bonds are absent. There are present in the ring system four pyrrole rings joined through the alpha positions of the respective pyrrole rings by a methine group, i.e., —CH═. The compounds of the present invention are designated as derivatives of the tetrapyrroles for convenience in the disclosure and the appended claims and it will be understood that the term "tetrapyrrole" will designate compounds of the characteristic ring structure designated hereinbefore as well as the corresponding perhydro derivatives, and the corresponding non-cyclic pyrroles, i.e., the linear tetrapyrroles, commonly known as the bile pigments.

The tetrapyrroles employed in the present invention are all derived by various means and various alteration procedures from natural tetrapyrroles. The naturally occurring tetrapyrroles have as their common ancestor uroporphyrinogen III, a hexahydroporphyrin reduced at the bridge positions. For example, synthetic or biosynthetic derivatives or products of protoporphyrins IX or protoporphyrinogen IX are well-known in the art (see, for example, Porphyrins and Metalloporphyrins, K. Smith Elsivier; The Porphyrins (vols. 1–7) D. Dolphin, Academic Press; and Biosynthetic Pathways, Vol. III, Chapter by B. Burnham, editor D. M. Greenberg, Academic Press).

The non-cyclic tetrapyrroles are commonly known as bile pigments and include, for example, bilirubin and biliverdin. These tetrapyrroles are also derived from protoporphyrin, e.g., as metabolic products in animals.

A further characteristic of the present new compounds is the presence of at least one amide linkage between the amino acid and a carboxy substituent on the ring structure. These are present in the instant new compounds together with other substiuents as defined hereinafter.

Thus, the present invention contemplates amino acid derivatives of compounds which contain the chromophore of porphyrins, chlorins or bacteriochlorins, as well as related porphyrin compounds. The amide linkage involves an amino group of the specified amino acid and a carboxy group of the tetrapyrrole. The present new compounds embrace, inter alia, derivatives of the tetrapyrroles which contain at least one free carboxy group. These derivatives include the major classes of tetrapyrroles: carboxy-containing porphyrins, chlorins, and bacteriochlorins, which are well-known to those skilled in this art.

The amino acids employed in the present invention have the following formula:

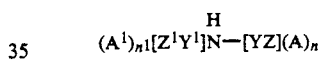

wherein A¹, n¹, Z¹, Y¹, Y, Z, A and n have the meanings described hereinabove. For purposes of this invention, it is intended that A can be a substituent on: Y or Z or both and that A¹ can be a substituent on Y¹ or Z¹ or both. The variables n and n¹ indicate the number of A and A¹ substituents present. For example, when n is 2, then each A which may be the same or different may be disubstituted on Y or Z or mono substituted on Y and Z. When n is 1, the A is monosubstituted on Y or Z, but not both. Finally, when n is 0, then (A)$_n$ is defined to mean hydrogen. Similarly, when n¹ is 2, then each A¹ which may be the same or different may be disubstituted on Y¹ or Z¹ or monosubstituted on Y¹ and Z¹. When n¹ is 1, then A¹ is monosubstituted on Y¹ or Z¹, but not both. Finally, when n¹ is 0, then (A₁)$_n$ is defined as hydrogen.

The amino acids employed in the present invention are primary or secondary amino acids. The specific position of the amino group in the carbon atom chain is not critical; the only requirement is that the amino group be available to form the requisite amide linkage with the carboxyl group of the selected prophyrin. When the amino acid is primary, it must contain at least one sulfonic acid group, i.e., SO₃H. It is to be understood that the sulfonic acid group is attached to the main chain through the sulfur atom. The primary amino acids contemplated to be used in the present invention have the formula:

α-sulfo-β-alanine is an example of this class of amino acids.

The secondary amino acids used in the present invention contain two of the following functional groups: COOH, SO₃H or OH, with the proviso that the amino compounds contain at least one COQH or SO₃H. In other words, the present invention does not employ those amino acids containing two hydroxy groups. On the other hand, the present invention employs those compounds containing two $CO_2H$ groups, two $SO_3H$ groups, one $CO_2H$ and one $SO_3H$, one $CO_2H$ and one OH group and one $SO_3H$ and one OH group.

Various secondary amino groups are used in the present invention. When n is 2, then the amino acids used in the present invention have two subgeneric formulae. One of the formulae is:

$$H\ Z^1Y^1-N-[YZ](A)_n$$

wherein $Y^1$, $Z^1$, Y, Z and A have the meanings described heretofore, and n is 2. In other words, both of the groups defined by A, i.e., $CO_2H$, $SO_3H$ or hydroxy are either substituted on Y, Z or both Y and Z. Compounds within this definition include N-alkyl-aspartic acids, N-alkyl-glutamic acid, N-alkyl serine or N-alkyl threonine and the like.

Another variation has the generic formula:

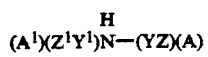

$$(A^1)(Z^1Y^1)N-(YZ)(A)$$

wherein $Z^1$, $Y^1$, Y, Z, $A^1$ and A have the aforementioned definitions. In this formulation, the A substituent is substituted on Y or Z and the $A^1$ substituent is substituted on $Z^1$ or $Y^1$. Examples include iminodiacetic acid, iminodiproponic acid, 4-hydroxyproline and the like.

It is to be noted that amino acids containing ring substituents are also employed in the present invention. For example, Y and $Y^1$ taken together with the N to which they are attached can form a N-heterocyclic containing 4–9 ring carbon atoms which may be saturated or partially unsaturated. The N-heterocyclic may be substituted or unsubstituted monocyclic or bicyclic rings any may contain up to a total of 15 carbon atoms. An example is 4-hydroxyproline.

Alternatively, YZ or $Y^1Z^1$ individually may form a ring containing from 5–10 ring carbon atoms and up to a total of 15 carbon atoms. These groups may be monocyclic or bicyclic or tricyclic. For example, Y and Z or $Y^1$ and $Z^1$ taken together may form a cyclopentyl, cyclohexyl, norbornyl, adamantyl and the like.

With respect to the alkylene groups Y, Z, $Y^1$ and $Z^1$, the lower alkylene groups contain up to 6 carbon atoms which may be in the normal or branched configuration including methylene, ethylene, propylene, isopropylene, butylene, isobutylene, hexylene, and the like. It is preferred that lower alkylene contains from 1–3 carbon atoms.

These amino acids may be substituted with angular alkyl groups, such as methyl and ethyl groups, as well as other groups which do not adversely affect the capability of the amino group to form the amide linkage, e.g., alkoxy groups, or acyloxy groups.

Exemplary compounds of the tetrapyrrole classes are illustrated in Table I in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

TABLE I

| | Ring Position | | | | | | | | | |
|---|---|---|---|---|---|---|---|---|---|---|
| | A | | B | | C | | | D | | |
| PORPHYRIN | 1 | 2 | 6 | 7 | 11 | 12 | 14 | 16 | 17 | Dihydro |
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me<br>\|<br>—CH<br>\|<br>OH | Me | Me<br>\|<br>—CH<br>\|<br>OH | Me | Pr | H | Pr | Me | — |
| Protoporphyrin IX | Me | V | Me | V | Me | Pr | H | Pr | Me | — |
| Photoprotoporphyrin IX (one of two isomers shown) | Me | V | {—Me<br>—OH | =CHCHO | Me | Pr | H | Pr | Me | 6,7 |
| Mesoporphyrin IX | Me | Et | Me | Et | Me | Pr | H | Pr | Me | — |
| Transmesochlorin IX | {H<br>Me | {H<br>Et | Me | Et | Me | Pr | H | Pr | Me | 1,2 |
| Transmesochlorin IX | Me | Et | {H<br>Me | {H<br>Et | Me | Pr | H | Pr | Me | 6,7 |
| Chlorin e₄ | Me | V | Me | Et | Me | CO₂H | Me | {H<br>Pr | {H<br>Me | 16,17 |
| Chlorin e₆ | Me | V | Me | Et | Me | CO₂H | Ac | {H<br>Pr | {H<br>Me | 16,17 |
| Mesochlorin e₄ | Me | Et | Me | Et | Me | CO₂H | Me | {H<br>Pr | {H<br>Me | 16,17 |
| Isochlorin e₄ | Me | V | Me | Et | Me | H | Ac | {H<br>Pr | {H<br>Me | 16,17 |
| Mesoisochlorin e₄ | Me | Et | Me | Et | Me | H | Ac | {H | {H | 16,17 |

TABLE I-continued

| | Ring Position | | | | | | | | | |
|---|---|---|---|---|---|---|---|---|---|---|
| | A | | B | | C | | | D | | |
| PORPHYRIN | 1 | 2 | 6 | 7 | 11 | 12 | 14 | 16 | 17 | Dihydro |
| Mesochlorin $e_6$ | Me | Et | Me | Et | Me | $CO_2H$ | Ac | Pr<br>H<br>Pr | Me<br>H<br>Me | 16,17 |
| Bacteriochlorin $e_6$ | Me | ACL | H<br>Me | H<br>Et | Me | $CO_2H$ | Ac | H<br>Pr | H<br>Me | 6,7<br>16,17 |
| Bacteriochlorin $e_4$ | Me | ACL | H<br>Me | H<br>Et | Me | $CO_2H$ | Me | H<br>Pr | H<br>Me | 6,7<br>16,17 |
| Bacterioisochlorin $e_4$ | Me | ACL | H<br>Me | H<br>Et | Me | H | Ac | H<br>Pr | H<br>Me | 6,7<br>16,17 |

Notes:
Me: —$CH_3$ (Methyl group)
Pr: —$CH_2CH_2COOH$ (Propionic acid group)
V: —CH=$CH_2$ (Vinyl group)
Et: —$CH_2CH_3$ (Ethyl group)
Ac: —$CH_2COOH$ (Acetic acid group)
ACL: $CH_3$—CO— (Acetyl group)

The preferred tetrapyrrole carboxylic acids are those wherein at least three carboxylic acid groups are present in the tetrapyrrole, preferably asymmetrically attached to the porphyrin ring system, e.g., the carboxylic acid groups are present on the rings A and B side of the molecule or on the rings D and C side of the molecule.

The particularly preferred tetrapyrroles used in this invention are those represented by the formula:

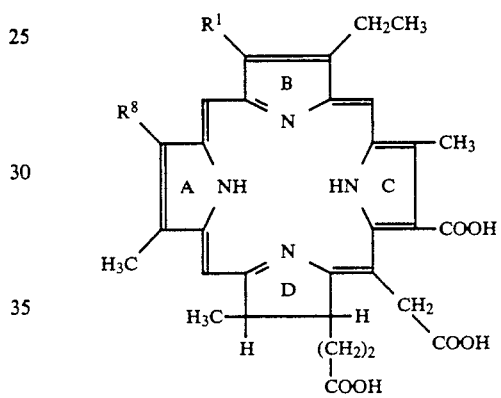

wherein
$R^8$=H, vinyl, ethyl, acetyl or formyl;
$R^1$=methyl or formyl;
and pharmaceutically-acceptable salts thereof.

Exemplary preferred tetrapyrroles are illustrated in Table II:

TABLE II

| | Ring Position | | | | | | | | | |
|---|---|---|---|---|---|---|---|---|---|---|
| | A | | B | | C | | | D | | |
| PORPHYRIN | 1 | 2 | 6 | 7 | 11 | 12 | 14 | 16 | 17 | Dihydro |
| Chlorin $e_6$ | Me | V | Me | Et | Me | $CO_2H$ | Ac | H<br>Pr | H<br>Me | 16,17 |
| Mesochlorin $e_6$ | Me | Et | Me | Et | Me | $CO_2H$ | Ac | H<br>Pr | H<br>Me | 16,17 |
| Bacteriochlorin $e_6$ | Me | ACL | H<br>Me | H<br>Et | Me | $CO_2H$ | Ac | H<br>Pr | H<br>Me | 6,7<br>16,17 |
| 2-Desvinylchlorin $e_6$ (or Deuterochlorin $e_6$) | Me | H | Me | Et | Me | $CO_2H$ | Ac | H<br>Pr | H<br>Me | 16,17 |
| 2-Acetylchlorin $e_6$ | Me | ACL | Me | Et | Me | $CO_2H$ | Ac | H<br>Pr | H<br>Me | 16,17 |
| 2-Formylchlorin $e_6$ | Me | CHO | Me | Et | Me | $CO_2H$ | Ac | H<br>Pr | H<br>Me | 16,17 |
| Rhodin $g_7$ | Me | V | CHO | Et | Me | $CO_2H$ | Ac | H<br>Pr | H<br>Me | 16,17 |

Notes:
Me: —$CH_3$ (Methyl group)
Pr: —$CH_2CH_2COOH$ (Propionic acid group)
V: —CH=$CH_2$ (Vinyl group)
Et: —$CH_2CH_3$ (Ethyl group)
Ac: —$CH_2COOH$ (Acetic acid group)
ACL: $CH_3$—CO— (Acetyl group)

The present new compounds form salts with either acids or bases. The acid salts are particularly useful for purification and/or separation of the final amide products as are the salts formed with bases. The base salts, however, are particularly preferred for diagnostic and therapeutic use as hereindescribed.

The acid salts are formed with a variety of acids such as the mineral acids, hydrochloric, hydrobromic, nitric and sulfuric acids; and organic acids such as tolunesulfonic and benzenesulfonic acids.

The base salts include, for example, sodium, potassium, calcium, magnesium, ammonium, triethylammonium, trimethylammonium, morpholine and piperidine salts and similar such salts.

The acid and base salts are formed by the simple expediency of dissolving the selected amino acid tetrapyrrole amide in an aqueous solution of the acid or base and evaporation of the solution to dryness. The use of a water-miscible solvent for the amide can assist in dissolving the amide.

The final amide products can also be converted to metal complexes for example by reaction with metal salts. The magnesium or other non triplet state quenching metal complexes may be useful for the same purpose as the adduct product. Other metal complexes, as well as the magnesium complex, including, for example, iron and zinc, are useful to preclude contamination during processing of the adduct product by metals such as nickel, cobalt and copper, which are difficult to remove. Zinc and magnesium are readily removed from the final adduct product after processing is completed.

Since many of the amino acids exist in both the D- and L-forms, and also are employed in mixtures of these forms as well as the D,L-form, the selection of the starting amino acid will, of course, result in products in which the respective isomer or mixture of isomers exist. The present invention contemplates the use of all such isomers, but the L-form is particularly preferred.

The present new compounds are prepared by the usual peptide synthetic routes which generally include any amide-forming reaction between the selected amino acid and the specific tetrapyrrole. Thus, any amide-forming derivative of the tetrapyrrole carboxylic acid can be employed in producing the present new peptides, e.g., lower alkyl esters, anhydrides and mixed anhydrides.

The preferred preparative methods use mixed anhydrides of the carboxylic acid or carbodiimides. The reactants are merely contacted in a suitable solvent therefor and allowed to react. Temperatures up to the reflux temperature can be used, with the higher temperatures merely reducing the reaction time. However, excessively high temperatures are usually not preferred so as to avoid unwanted secondary reactions.

The procedures for forming the instant amides are well known in this art and are provided in detail in the accompanying examples.

Since the selected tetrapyrrole adducts contain more than one carboxyl group, mixtures of products can be formed including isomeric di- and even tri- or higher amide products, depending on the number of carboxyl groups and depending on the selected stoichiometry. Thus when equivalent mixtures of amino acid and tetrapyrrole are reacted, the product contains monoamides, but, also present will be di- or poly amides. It is generally possible to separate the monoamides and higher amides using known chromatographic techniques and crystallization techniques. In some cases, however, the mixtures may be as effective as the pure compounds.

Usually, unreacted tetrapyrrole adducts are separated from the peptide products of the invention during purification as, for example, by chromatographic techniques.

The tetrapyrroles used in the present invention are commercially available or can be produced by art recognized techniques known to one skilled in the art, as described on Pages 3 and 4, supra and Pages 24–25, infra.

The amino acids used in the present invention are commercially available or can be produced by art recognized techniques known to one skilled in the art. An exemplary procedure for preparing the amino acids is through simple substitution reactions.

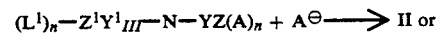

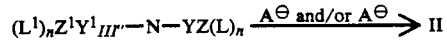

wherein n, $n^1$, $Z^1$, $Y^1$, Y and Z have the forementioned meanings and A or $A^1$ are $OH^\ominus$ or $SO_3^\ominus$ L and $L^1$ are good leaving groups, such as halides, brosylates, mesylates, tosylates and the like.

The carboxy groups can be added to the amino acids by replacing A or A' with $CN^\ominus$ followed by acid hydroloysis Alternatively, a carboxy substituent can be formed by reacting $CO_2$ or dry ice with a Grignard reagent in ethers such as diethyl ether or tetrahydrofuran. The reaction can be run at room temperature up to reflux temperatures of the solvent. The Grignard reaction should be run prior to the addition of the hydroxy or carboxy substituent to the molecule.

Alternatively, II can be prepared by reacting the halide of Formula IV with an excess of amine of Formula V as follows under amine alkylation conditions:

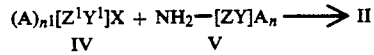

wherein $A^1$, $n^1$, $Z^1$, $Y^1$, Z, Y, A and n have the aforementioned meanings and X is halide.

Alternatively, II can be prepared by reacting an amine of Formula Y with an aldehyde of Formula VI and then reducing the corresponding imine that is formed with an hydrogenating catalyst such as $H_2/Ni$, $H_2/Pt$ or $H_2/Pd$ using techniques known to one skilled in the art:

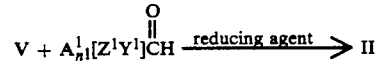

Except for the Grignard reaction indicated hereinabove, the reactions described hereinabove are normally effected at or near room temperature, although temperatures from 0° C. up to the reaction medium can be employed. The reaction is carried out in a solvent that will dissolve both reactants and is inert to both as well. Solvents such as methylene chloride, diethyl ether, tetrahydrofuran, dioxane, chloroform and the like can be employed.

Photodiagnosis and Phototherapy

The compounds of the present invention are useful for the photodiagnosis and phototherapy of tumor, cancer and malignant tissue (hereinafter referred to as "tumor").

When a man or animal having tumor is treated with doses of a compound of the present invention and when appropriate light rays or electromagnetic waves are applied, the compound emits light, i.e., fluorescence. Thereby the existence, position and size of tumor can be detected, i.e., photodiagnosis.

When the tumor is irradiated with light of proper wavelength and intensity, the compound is activated to exert a cell killing effect against the tumor. This is called "phototherapy".

Compounds intended for photodiagnosis and phototherapy ideally should have the following properties:

(a) non-toxic at normal therapeutic dosage unless and until activated by light;

(b) should be selectively photoactive;

(c) when light rays or electromagnetic waves are applied, they should emit characteristic and detectable fluorescence;

(d) when irradiated with light rays or electromagnetic waves are applied, they are activated to an extent to exert a cell killing effect against tumor; and (e) easily metabolized or excreted after treatment.

The present new compounds possess greater fluorescence in tumors than do the corresponding basic tetrapyrroles. Their use provides the best contrast in tumors compared to normal tissue around the tumor. The instant compounds absorb activating energy for phototherapy in the convenient range of 600 to 800 nanometers, with the preferred compounds absorbing in the 620–760 nanometer range, i.e., light of longer wavelengths which more readily permits penetration of energy into the tumor for phototherapeutic purpose.

In present experience, the present compounds more uniformly distribute throughout the tumor than the basic tetrapyrrole permitting the use of considerably lower dosage (to about 1/10th of the required normal dose of the basic tetrapyrrole) which lessens, if not eliminates, photosensitization in the host. They also possess a more consistent fluorescence whereas some of the corresponding tetrapyrroles snow inconsistent fluorescence or the fluorescence varies from day to day in the host.

A particularly advantageous property of the present compounds resides in the ease with which they are excreted by the host. Generally, within 48 to 72 hours of intravenous or intraperitoneal administration, there are little or not detectable amounts in normal muscle tissue. The present compounds which are excreted with their chromophore intact are recovered from the feces of the host within 48–72 hours of injection. Under equivalent circumstances, substantial amounts of the corresponding tetrapyrroles remain, as compared with only minor amounts of peptides formed with the aminocarboxylic acids remain in the host, e.g., up to about 20%. This property is extremely important in that it contributes to minimization of photosensitization of the host.

The instant compounds can be used for diagnosis and therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkins's disease, multiple myeloma, renal cancer, leukemia, and malignant lymphocytoma. For diagnosis, the sole requirement is that the tumor be capable of selectivity fluorescing when exposed to proper light. For treatment, the tumor must be penetrable by the activation energy. For diagnosis, light of shorter wavelength is used whereas for therapeutic purposes light of longer wavelength is used to permit ready penetration of the tumor tissue. Thus, for diagnosis, light of from 360–760 nanometers can be used, and for treatment, from 620–760, depending on the individual characteristics of the tetrapyrrole. The absorption characteristics of the present new compounds are substantially the same as the tetrapyrrole from which derived.

It is necessary that the light rays be so intense as to cause the compounds to emit fluorescence for diagnosis and to exert a cell killing effect for therapy.

The source of irradiation for photodiagnosis and phototherapy is not restricted, however, but the laser beam is preferable because intensive light rays in a desired wavelength range can be selectively applied. For example, in photodiagnosis, the compound of the invention is administered to a human or animal body, and after a certain period of time, light rays are applied to the part to be examined. When an endoscope can be used for the affected part, such as lungs, gullet, stomach, womb, unrinary bladder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser beams from the tip of quartz fibers. Besides the irradiation of the surface of tumor, the internal part of the tumor can be irradiated by inserting the tip of quartz fibers into the tumor. The irradiation can be visually observed or imaged on a CRT screen.

For photodiagnosis, light of wavelengths between 360 and 760 nm. is suitable for activating the present tetrapyrrole compounds. Of course, each compound has a specific optimal wavelength of activation. A long wavelength ultraviolet lamp is particularly suitable for photodiagnosis. Similar methods for viewing of the treated tumor can be used as already described for phototherapy.

The dosages of the present new compounds will vary depending on the desired effect, whether for diagnosis or for treatment. For diagnosis, doses of as little as 1 mg/kg will be effective, and up to about 20 mg/kg can be used. For treatment, the dose will usually approximate about 5 mg/kg. Of course, the dosage for either diagnosis or treatment can be varied widely in view of aforesaid advantageous properties of the present compounds, e.g., the ease of elimination from the host, for one.

The present compounds are apparently non-toxic at the dosage levels employed for diagnosis or treatment. No mortality of test animals due the present compounds has been noted in studies employing dosage levels up to 100 mg/kg.

For both diagnosis and treatment, the present compounds can be administered by the oral, intravenous, or intramuscular routes. They can be formulated as lyophilized sterile, pyrogen-free compounds, preferably in the form of basic salts, e.g., sodium salt. The preferred dosage forms are provided as injectable solutions (isotonic).

The irradiation source used in treatment of tumors containing compounds of this invention is a filtered, high-intensity, continuous source or pumped dye, or other laser and light delivery system, which is capable of performing within the following limits: power intensity 20–500 mw/cm$^2$ at wavelengths between 620 and 760 nm. and a total output of at least 500 mw. or greater. Several currently commercially available lasers meet these criteria.

The tetrapyrroles can be prepared by various synthetic methods which are found in the literature, e.g., Pheophorbides Willstatter, R., Stoll, A.; *Investigations on Chlorophyll*, (Transl. Schertz, F. M. M., Merz, A. R.) p. 249. Science Printing Press Lancaster, Pa. 1928.

Pennington, F. C. Strain, H. H., Svec, W. A., Katz, J. J.; *J. Amer. Chem. Soc.* 86, 1418 (1964).

Chlorin $e_6$

Willstatter, R. Stoll, A.; *Investigations on Chlorophyll*, (Trans., Schertz, F. M., Merz, A. R.,) p. 176. Science Printing Press, Lancaster, Pa., 1928.

Willstatter, R., Isler, M.; *Ann. Chem.*, 390, 269 (1912).

Fisher, H., Braumler, R.; *Ann. Chem.*, 474, 65 (1929).

Fisher, H., Siebel, H.; *Ann. Chem.*, 499, 84 (1932).

Conant, J. B., Mayer, W. W.; *J. Amer. Chem. Soc.*, 52, 3013 (1930).

Chlorin $e_4$

Fisher, H., Heckmaier, J., Plotz, E.; *Justus Leibics Ann. Chem.*, 500, 215 (1933).

Chlorin $e_6$, $e_4$, isochlorin $e_4$, mesochlorin $e_6$, bacteriopheneophorbide, bacteriochlorin $e_6$ Fischer and Orth, "Des Chemie des Pyrrole" *Akademische Verlazscesellschaft, Leipzig*, 1940, Vol. II, Part 2.

General Reference for Porphyrins

"Porphyrins and Metalloporphyrins" ed. Keven M. Smith, Elsevier 1975 N.Y.

The compounds of the present invention can be administered to the host in a variety of forms adapted to the chosen route of administering, i.e., orally, intravenously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elexirs, suspensions, syrups, wafers, and the life. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present new compounds may also be applied directly to tumors, whether internal or external, in the host in topical compositions. Exemplary compositions include solutions of the new compounds in solvents, particularly aqueous solvents, most preferably water. Alternatively, for topical application particularly to skin tumors, the present new compounds may be dispersed in the usual cream or salve-formulations commonly used for this purpose or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic end absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples further illustrate the invention.

EXAMPLE 1

Mono iminodiacetic acid Chlorin $e_6$ 500 mg chlorin $e_6$ was stirred in 5 ml of dimethyl formamide until dissolved (approximately 10 minutes).1 150 mg of 1-ethyl-3-(3-dimethylamino-propyl) carbodiimide was added and the mixture allowed to stir for one hour. At this time, 5 ml of a 0.5M solution of iminodiacetic acid of 1M sodium acetate, the pH of which was adjusted 9 with sodium hydroxide, was added to the dimethylformamide solution.

The mixture was allowed to stir for 2 hours, then diluted to 50 ml with 0.1N NaOH, the pH adjusted to 7 with dilute HCl, and the solution applied to a reverse phase (Prep C-18 silica) column (4 cm × 60 cm). The column was eluted with 20 to 35% MeOH in 0.01M $NaPO_4$ pH 6.85 buffer. The methanol was removed from the fractions containing the conjugated product (first to elute from the column) by rotary evaporation.

The product was precipitated at pH 3 with HCl, collected by centrifugation and washed twice at the centrifuge with pH 3 water. The sample was dissolved with 0.1N sodium hydroxide at pH 9, and lyophilized to dryness as the tetra sodium salt .X hydrate. Yield 70 mg.

EXAMPLE 2

Mono-N-methyl-L-glutamyl chlorin $e_6$ 250 mg of chlorin $e_6$ was stirred in 3 ml of dimethylformamide until dissolved (approximately 10 minutes). 75 mg of 1-ethyl-3-(3-dimethylaminopropyl) carbodiimide was added and the mixture allowed to stir for 30 minutes. 100 mg of N-methyl-L-glutamic acid was then added along with 7 ml more dimethylformamide. The mixture was allowed to react for three hours. At this time, the TLC (70% MeOH 30% 0.01M $NaPO_4$ pH 6.85 on C-18 plates) showed about 40 percent product.

The solution was then diluted with 25 ml of 1M sodium acetate solution and the pH of this solution was adjusted to 9 with sodium hydroxide. After all precipitate was dissolved, the solution was placed on a 2.5 × 30 cm reverse phase (Prep C-18 silica) column and eluted with 20–40% methanol in 0.01M $NaPO_4$ pH 6.85 buffer. The fractions containing the pure product as ascertained by TLC were reduced in volume to approximately 400 ml and collected by running through a small amount of reverse phase packing on a 5 cm buchner funnel. The packing was washed with water, then the product eluted with methanol. The methanol was removed by flash evaporation and the remaining aqueous solution of approximately 20 ml volume was adjusted to pH 9 with sodium hydroxide, filtered and lyophilized.

The tetra sodium salt was dissolved in 2 ml of water, filtered to remove silica, then crystallized by slow addition of approximately 10 ml of dimethylformamide. The product was filtered, washed with dimethylformamide, then acetone, then dried under vacuum. Yield 136 mg of the tetrasodium salt .X hydrate.

EXAMPLE 3

Mono N-methyl(D,L)aspartyl chlorin $e_6$ 500 mg of chlorin $e_6$ was stirred until dissolved in 5 ml of dimethyl formamide (approximately 10 minutes). 160 mg of 1-ethyl-3-(3-dimethylaminopropyl) carbodiimide was added and the mixture allowed to stir for 15 minutes. 200 mg of N-methyl(D,L)aspartic acid was then added and the mixture was stirred for 3 hours.

50 ml of 1M sodium acetate solution was then added, and the pH adjusted to 9. The solution was stirred until all solid was dissolved and then added to a 4 cm × 60 cm reverse phase (Prep. C-18 silica) column. The column was eluted with 20 to 40% methanol in 0.01M $NaPO_4$ pH 6.85. The fractions containing the pure product as ascertained by TLC (70% MeOH, 30% 0.01M $NaPO_4$ pH 6.85 C-18 reverse phase palte) were pooled and reduced in volume to approximately 100 ml by flash evaporation.

The product was precipitated at pH 3, collected by centrifugation, washed twice with pH 3 water at the centrifuge, and dissolved at pH 9 with 0.1N sodium hydroxide. The solution was dried by lyophilization yielding 230 mg of the tetrasodium salt .X hydrate.

EXAMPLE 4

Mono iminodipropionic acid chlorin $e_6$

Crude iminodipropionic acid was prepared by hydrolysis of iminodipropionitrile in refluxing 6N hydrochloric acid and extracting a basic aqueous solution with n-butanol to remove unhydrolyzed product, then extracting iminodipropionic acid into n-butanol from the aqueous solution adjusted to pH 3. This crude preparation dired from the n-butanol was used in coupling to chlorin $e_6$ with final purification based upon chromatography of the chlorin $e_6$ conjugates.

800 mg of chlorin $e_6$ was dissolved with stirring in 8 ml of dimethylformamide. 265 mg of 1-ethyl-3-(3-dimethylaminopropyl) carbodiimide was then added, and the mixture was allowed to stir for 30 minutes. 600 mg of the crude preparation of iminodipropionic acid was added as solid, and the mixture allowed to stir at r.t. for 16 hours. TLC by reverse phase chromatography (C-18 plate) 70% MeOH 30% 0.01M NaPO$_4$ pH 6.85 showed approximately 10 to 20% product which has a higher R$_f$ value than the chlorin e$_6$ and the rest was chlorin e$_6$ and a slower running derivative of chlorin e$_6$.

The DMF solution was diluted with 100 ml of 0.1N sodium hydroxide and the pH adjusted to 9 and stirred until allsolid had dissolved. The solution was then added to a 4 cm×60 cm reverse phase (Prep. C-18 silica) column. The column was eluted tih 30–40% MeOH in 0.01M NaPO$_4$ pH 6.85. The fractions collected were pooled according to their purity as ascertained by TLC, reduced in volume to approximately 100 ml by flash evaporation and precipitated at pH 3 with HCl.

The precipitate was collected by centrifugation and washed with pH 3 water 3 times at the centrifuge. The precipitate was then dissolved in approximately 10 ml of water by titrating to pH 9 with dilute sodium hydroxide. The product was then frozen and lyophilized to dryness. Yield 60 mg of tetrasodium salt .X hydrate.

EXAMPLE 5

Mono trans-4-hydroxy-L-proline-chlorin e$_6$ 300 mg of chlorin e$_6$ was dissolved in 3 ml of dimethylformamide with stirring (approximately 10 minutes); 96 mg of 1-ethyl-3-(3-dimethylaminopropyl) carbodiimide was then added and the mixture allowed to stir for 30 minutes. At this time 198 mg of finely powdered trans-4-hydroxy-L-proline was added, and the mixture allowed to stir at room temperature for 3 hours.

The dimethyl formamide solution was poured into 30 ml of 0.1N sodium hydroxide solution and stirred until dissolved. 10 ml of 1M NaPO$_4$ pH 6.85 buffer was added and the solution applied to a 2.5 cm×30 cm (Prep. C-18 silica) column. The column was eluted with 30–40% MeOH in 0.01M NaPO$_4$ pH 6.85 buffer. The pure fractions as ascertained by TLC reverse phase (C-18) plates 70/30 MeOH/0.01M NaPO$_4$ pH 6.85 were combined and reduced in volume to 100 ml by flash evaporation.

The product was precipitated at pH 3, washed 3 times at the centrifuge with pH 3 water and redissolved in 10 ml of water by titrating to pH 10 with sodium hydroxide. The product was then precipitated by addition of approximately 30 ml of dimethyl formamide and then 30 ml of acetone. The product was collected by centrifugation and washed once with dimethyl formamide and twice with acetone at the centrifuge. The product was then dired under vacuum. Yield 90 mg of the trisodium salt .X hydrate.

EXAMPLE 6

Mono α-sulfo-β-alanyl chlorin e$_6$ 500 mg of chlorin e$_6$ was dissolved in 10 ml of dimethylformamide with stirring (approximately 10 minutes). 150 mg of 1-ethyl-3-(3-dimethylaminopropyl) carbodiimide was added and the mixture was stirred for an additional 30 minutes. At this time, 10 ml more dimethylformamide was added, and the activated chlorin e$_6$ was added to 50 ml of 0.5M sodium acetate containing 400 mg of dissolved αsulfo βalanine, adjusted to pH 10 with sodium hydroxide. The mixture was stirred for 1 hour at room temperature.

The solution was then applied to a 4×60 cm reverse phase (Prep C-18 silica) column and eluted with 30 to 40% methanol in 0.01M NaPO$_4$ pH 6.85. The pure fractions as ascertained by TLC (C-18 plate) 70/30 MeOH/0.01M NaPO$_4$ pH 6.85 buffer were pooled and reduced to approximately ¼ of their volume by flash evaporation. The product was applied to C-18 packing in a 7 cm Buchner funnel, washed with water, then eluted form the packing with 50/50 MeOH/H$_2$O. The methanol was removed by flash evaporation and the remaining aqueous solution lyophilized. The solid was redissolved in 10 ml of water and filtered to remove silica. The aqueous solution was lyophilized again and yielded 350 mg of the tetrasodium salt .X hydrate.

EXAMPLE 7

Mono N-methyl-L-serinyl chlorin e$_6$ 600 mg of chlorin e$_6$ was dissolved in 6 ml of dimethylformamide and stirred for 20 minutes. 192 mg of 1-ethyl-3-(3-dimethylaminopropyl) carbodiimide was added and the mixture allowed to stir for 45 minutes. 400 mg of finely powdered N-methyl-L-serine was added and the mixture stirred for 20 hours at room temperature.

The dimethylformamide solution was poured into 60 ml of 0.1N sodium hydoxide and allowed to stir for 15 minutes. 20 ml of 1M NaPO$_4$ pH 6.85 was added, and the solution was applied to a 4×45 cm (Prep. C-18 silica) column. The column was eluted with 30–45% MeOH in 0.01M NaPO$_4$ pH 6.85 buffer. The pure fractions as ascertained by TLC (C-18 plate) in 70/30 MeOH/0.01M NaPO$_4$ pH 6.85 buffer were pooled, and the methanol removed by flash evaporation. The product was collected on preparative C-18 packing in a 9 cm Buchner funnel, washed with water, and eluted off the packing with 50/50 MeOH/H$_2$O. The methanol was removed by flash evaporation and the product was dried by lyophilization. Yield 350 mg of the trisodium salt .X hydrate.

EXAMPLE 8

By substituting L-threonine for serine in Example 7, and using the procedure described therein, Mono N-methyl-L-threoninyl chlorin e$_6$ is prepared.

EXAMPLE 9

Similarly by substituting transmescholin IX for chlorin e$_6$ in Example 8, the following compounds can be prepared:
Mono iminodiacetic acid transmesochlorin IX
Mono N-methyl-L-glutamyl transmesochlorin IX
Mono N-methyl(D,L)aspartyl transmesochlorin IX
Mono iminodipropionic acid transmesochlorin IX
Mono trans-4-hydroxy-L-proline transmesochlorin IX
Mono α-sulfo-β-alanyl transmesochlorin IX
Mono N-methyl-L-serinyl transmesochlorin IX
Mono N-methyl-L-threoninyl transmesochlorin IX

EXAMPLE 10

Similarly by substituting protoporphyrin IV for chlorin e$_6$ in Examples 1-8, the following compounds can be preprared:
Mono-iminodiacetic acid protoporphyrin IX
Mono-N-methyl-L-glutamyl protoporphyrin IX
Mono-N-methyl(D,L)aspartyl protoporphyrin IX Mono iminodipropionic acid protoporphyrin IX
Mono-trans-4-hydroxy-L-proline protoporphyrin IX
Mono α-sulfo-β-serinyl protoporphyrin IX
Mono N-methyl-L-serinyl protoporphyrin IX
Mono N-methyl-L-threoninyl protoporphyrin IX

EXAMPLE 11

Similarly, by substituting mesoporphyrin IX for chlorin $e_6$ in Examples 1-8, the following compounds can be prepared:
Mono iminodiacetic acid mesoporphyrin IX
Mono N-methyl-L-glutamyl mesoporphyrin IX
Mono N-methyl(D,L)aspartyl mesoporphyrin IX
Mono trans-4-hydroxy-L-proline mesoporphyrin IX
Mono α-sulfo-β-alanyl mesoporphyrin IX
Mono N-methyl-L-serinyl mesoporphyrin IX
Mono N-methyl-L-threoninyl mesoporphyrin IX

EXAMPLE 12

Similarly, by substituting pyropheophorbide a for chlorin $e_6$ in Examples 1-8, the following compounds can be prepared:
Mono iminodiacetic acid pyropheophorbide a
Mono N-methyl-L-glutamyl pyropheophorbide a
Mono N-methyl(D,L)aspartyl pyropheophorbide a
Mono trans-4-hydroxy-L-proline pyropheophorbide a
Mono α-sulfo-β-alanyl pyropheophorbide a
Mono N-methyl-L-serinyl pyropheophorbide a
Mono N-methyl-L-threoninyl pyropheophorbide a

EXAMPLE 13

Similarly, by substituting coproporphyrin III for chlorin $e_6$ in Examples 1-8, the following compounds can be prepared:
Mono iminodiacetic acid coproporphyrin III
Mono N-methyl-L-glutamyl coproporphyrin III
Mono N-methyl(D,L)aspartyl coproporphyrin III
Mono trans-4-hydroxy-L-proline coproporphyrin III
Mono α-sulfo-β-alanyl coproporphyrin III
Mono N-methyl-L-serinyl coproporphyrin III
Mono N-methyl-L-threoninyl coproporphyrin III

EXAMPLE 14

Similarly, by substituting deuteroporphyrin IX for chlorin $e_6$ in Examples 1-8, the following compounds can be prepared:
Mono iminodiacetic acid deuteroporphyrin IX
Mono N-methyl-L-glutamyl deuteroporphyrin IX
Mono N-methyl(D,L)aspartyl deuteroporphyrin IX
Mono trans-4-hydroxy-L-proline deuteroporphyrin IX
Mono α-sulfo-β-alanyl deuteroporphyrin IX
Mono N-methyl-L-serinyl deuteroporphyrin IX
Mono N-methyl-L-threoninyl deuteroporphyrin IX

EXAMPLE 15

Similarly, by substituting hematoporphyrin IX for chlorin $e_6$ in Examples 1-8, the following compounds can also be prepared
Mono iminodiacetic acid hematoporphyrin IX
Mono N-methyl-L-glutamyl hematoporphyrin IX
Mono N-methyl(D,L)aspartyl hematoporphyrin IX
Mono trans-4-hydroxy-L-proline hematoporphyrin IX
Mono α-sulfo-β-alanyl hematoporphyrin IX
Mono N-methyl-L-serinyl hematoporphyrin IX
Mono N-methyl-L-threoninyl hematoporphyrin IX

EXAMPLE 16

Similarly, by substituting mesochlorin $e_6$ for chlorin $e_6$ in Examples 1-8, the following compounds can be prepared:
Mono iminodiacetic acid mesochlorin $e_6$
Mono N-methyl-L-glutamyl mesochlorin $e_6$
Mono N-methyl(D,L)aspartyl mesochlorin e
Mono trans-4-hydroxy-L-proline mesochlorin $e_6$
Mono α-sulfo-β-alanyl mesochlorin e
Mono N-methyl-L-serinyl mesochlorin $e_6$
Mono N-methyl-L-threoninyl mesochlorin $e_6$

EXAMPLE 17

Similarly, by substituting bacteriochlorin $e_6$ for chlorin $e_6$ in Examples 1-8, the following compounds can also be prepared:
Mono iminodiacetic acid bacteriochlorin $e_6$
Mono N-methyl-L-glutamyl bacteriochlorin $e_6$
Mono N-methyl(D,L)aspartyl bacteriochlorin $e_6$
Mono trans-4-hydroxy-L-proline bacteriochlorin $e_6$
Mono α-sulfo-β-alanyl bacteriochlorin $e_6$
Mono N-methyl-L-serinyl bacteriochlorin $e_6$
Mono N-methyl-L-threoninyl bacteriochlorin $e_6$

EXAMPLE 18

Similarly, by substituting deuterochlorin $e_6$ for chlorin $e_6$ in Examples 1-8, the following compounds can be prepared:
Mono iminodiacetic acid deuterochlorin $e_6$
Mono N-methyl-L-glutamyl deuterochlorin $e_6$
Mono N-methyl(D,L)aspartyl deuterochlorin $e_6$
Mono trans-4-hydroxy-L-proline deuterochlorin e
Mono α-sulfo-β-alanyl deuterochlorin $e_6$
Mono N-methyl-L-serinyl deuterochlorin $e_6$
Mono N-methyl-L-threoninyl deuterochlorin $e_6$

EXAMPLE 19

Similary, by substituting 2-acetylchlorin e for chlorin $e_6$ in Examples 1-8, the following compounds can also be prepared:
Mono iminodiacetic acid 2-acetylchlorin $e_6$
Mono N-methyl-L-glutamyl 2-acetylchlorin $e_6$
Mono N-methyl(D,L)aspartyl 2-acetylchlorin $e_6$
Mono trans-4-hydroxy-L-proline 2-acetylchlorin $e_6$
Mono α-sulfo-β-alanyl 2-acetylchlorin $e_6$
Mono N-methyl-L-serinyl 2-acetylchlorin $e_6$
Mono N-methyl-L-threoninyl 2-acetylchlorin $e_6$

EXAMPLE 20

Similarly, by substituting 2-formylchlorin $e_6$ for chlorin $e_6$ in Examples 1-8, the following compounds can also be prepared:
Mono iminodiacetic acid 2-formylchlorin $e_6$
Mono N-methyl-L-glutamyl 2-formylchlorin $e_6$
Mono N-methyl(D,L)aspartyl 2-formylchlorin $e_6$
Mono trans-4-hydroxy-L-proline 2-formylchlorin e
Mono α-sulfo-β-alanyl 2-formylchlorin $e_6$
Mono N-methyl-L-serinyl 2-formylchlorin $e_6$
Mono N-methyl-L-threoninyl 2-formylchlorin $e_6$

EXAMPLE 21

Similarly, by substituting rhodin $g_7$ for chlorin $e_6$ in Examples 1-8, the following compounds can also be prepared:
Mono iminodiacetic acid rhodin $g_7$
Mono N-methyl-L-glutamyl rhodin $g_7$
Mono N-methyl(D,L)aspartyl rhodin $g_7$ Mono trans-4-hydroxy-L-proline rhodin $g_7$
Mono α-sulfo-β-alanyl rhodin $g_7$
Mono N-methyl-L-serinyl rhodin $g_7$
Mono N-methyl-L-threoninyl rhodin $g_7$ Physical characteristics of the compounds (relative polarity) is measured by a standard chromatographic system. The chromatographic data (Rf values) were measured on Baker silica gel-C18 thin layer chromatographic plates, the particle size of which is 20 uM, and the coating thickness of which is 200 uM. The solvent system for these chromatographic runs consisted of 75% methanol, and 25% 0.01M potassium phosphate buffer, pH 6.85. The Rf values for the various derivatives are tabulated in Table III.

TABLE III

PHYSICAL CHARACTERISTICS OF REPRESENTATIVE COMPOUNDS (RELATIVE POLARITY) AS MEASURED BY A STANDARD CHROMATOGRAPHIC SYSTEM
TLC Plate Baker Si-C18   20 um particle size
200 um coating thickness   Solvent system   75% methanol
25% 0.01 M KPO$_4$ Buffer pH 6.85

| Compound | $R_f$ |
|---|---|
| 1. Mono iminodipropionic acid chlorin $e_6$ | 0.76 |
| 2. Mono iminodiacetic acid chlorin $e_6$ | 0.81 |
| 3. Mono N-methyl (L)-glutamyl chlorin $e_6$ | 0.73 |
| 4. Mono N-methyl (D, L) aspartyl chlorin $e_6$ | 0.73 |
| 5. Mono N-methyl (L) serinyl chlorin $e_6$ | 0.73 |
| 6. Mono αsulfo β alanyl chlorin e $_6$ | 0.76 |
| 7. Mono trans-4-hydroxy (L) proline chlorin $e_6$ | 0.77 |

The preparation of pharmacological dosages for the administration of the active ingredient, that is the amino acid porphyrin adducts, which were prepared in Examples 1–21 hereinabove, is as follows:

EXAMPLE 22

A tablet base was prepared by blending the following ingredient in the proportion by weight indicated:

| | Grams |
|---|---|
| Sucrose, USP | 80.3 |
| Tapioca Starch | 13.2 |
| Magnesium Stearate | 4.4 |

Into this base, there was blended sufficient amino acid porphyrin adducts to provide tablets each containing 100 mg. of active ingredient.

EXAMPLE 23

A blend was prepared containing the following ingredients:

| | |
|---|---|
| Calcium phosphate | 17.6 |
| Dicalcium phosphate | 18.8 |
| Magnesium trisilicate, USP | 5.2 |
| Lactose, U.S.P. | 5.2 |
| Potato Starch | 5.2 |
| Magnesium Stearate A | 0.8 |
| Magnesium Stearate B | 0.32 |
| Porphyrin Amino Acid Adducts | 20 |

This blend was divided and formed into capsules each containing 25 mg of active ingredient.

The following protocols describes the procedure for the use of the compounds of the present invention in the treatment of mice tumors.

EXAMPLE 24

The photodynamic therapy experiments have been carried out on DBA/2 Ha Ros-d +Ha mice, using the transplantable tumor SMT-F. The procedure is as follows:

DBA/2 Ha Ros-d+Ha mice with SmT-F transplanted tumors in either the exterior part of the hind leg or the side of the mouse were injected intravenously via the external jugular or intraperitoneally with the photosensitizing drug. At the specified time after injection, the area over the tumor was shaved and the light treatment begun.

Light from a Cooper Aurora pumped tunable dye laster was administered via a micro lens system. The optical properties of the lens are such that the light exits the lens in a circular pattern with homogenous intensity throughout the lighted area. The diameter of the lighted area is a function of the distance from the lens.

The light intensity was measured with a Yellow Springs Instrument Model 65A Radiometer at the point of treatment. A 1.5 cm diameter circle of the animal's skin, centered as closely as possible over the tumor, was irradiated in all the experiments. The intensity, wavelength, and dosage of light is included in the data for individual groups of animals. Wavelengths are adjusted, using a Hartridge reversion spectroscope to within 1 nm of the stated value.

Twenty four hours after light treatment, each mouse received 5 mg of Evans Blue Dye intraperitoneally. After an additional two hours, the mice were sacrificed and the tumors were sectioned vertically through the center of the light treated area. Unaffected tumor was stained blue as was unaffected normal tissue. Necrotic or affected areas were white or red in appearance. Measurements on both the whole tumors and affected areas of the tumors were made vertically and horizontally with calipers to the nearest one half millimeter.

The results for representative compounds are indicated on the following pages.

Compound used in this group is - Trans-4-Hydroxy-L-Proline Chlorin E6
A 0 (zero) or no denotes that parameter was not observed.

| 1 GROUP # | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 102 | 1 | m | 29.9 | 100.0 | iv | 24.0 | satf | r. leg | 200.0 | 300.0 | 665 | 2.30 | 1.70 | 1.00 | 2.10 | 1.60 | 1.30 | 0.90 | 0.80 | 0.20 | Skin effect .8 × .8 |
| 102 | 2 | m | 27.8 | 100.0 | iv | 24.0 | satf | r. leg | 200.0 | 300.0 | 665 | 1.75 | 1.50 | 1.00 | 2.20 | 1.70 | 1.25 | 1.00 | 1.00 | 0.40 | Skin effect 1.0 × .9 |
| 102 | 3 | m | 27.9 | 100.0 | iv | 24.0 | satf | r. leg | 200.0 | 300.0 | 665 | 1.80 | 1.60 | 1.00 | 2.10 | 1.80 | 1.33 | 1.40 | 1.00 | 0.40 | Skin effect 1.1 × .4 |
| 102 | 4 | m | 30.1 | 100.0 | iv | 24.0 | satf | r. leg | 200.0 | 300.0 | 665 | 1.60 | 2.00 | 0.95 | 1.80 | 2.00 | 1.10 | 0.00 | 0.00 | 0.00 | No effect |
| 102 | 5 | m | 29.6 | 100.0 | iv | 24.0 | satf | r. leg | 200.0 | 300.0 | 665 | 1.75 | 1.20 | 0.80 | 2.50 | 1.60 | 1.20 | 1.30 | 1.05 | 0.30 | Skin effect 1.2 × 1.2 |
| 102 | 6 | m | 29.3 | 100.0 | iv | 24.0 | satf | r. leg | 200.0 | 300.0 | 665 | 2.15 | 1.75 | 1.05 | 2.10 | 1.70 | 1.10 | 1.20 | 1.00 | 0.20 | |
| 102 | 7 | m | 28.7 | 100.0 | iv | 24.0 | satf | r. leg | 200.0 | 300.0 | 665 | 2.10 | 1.50 | 1.00 | 2.20 | 1.80 | 1.20 | 0.80 | 0.80 | 0.15 | Skin effect .4 × .4 |
| 102 | 8 | m | 29.4 | 100.0 | iv | 24.0 | satf | r. leg | 200.0 | 300.0 | 665 | 1.75 | 1.40 | 1.00 | 1.75 | 1.60 | 0.90 | 0.00 | 0.00 | 0.00 | No effect |
| 102 | 9 | m | 28.2 | 100.0 | iv | 24.0 | satf | r. leg | 200.0 | 300.0 | 665 | 2.35 | 1.70 | 1.30 | 1.80 | 1.50 | 1.10 | 0.30 | 0.30 | 0.30 | |
| 102 | 10 | m | 29.1 | 100.0 | iv | 24.0 | satf | r. leg | 200.0 | 300.0 | 665 | 2.70 | 2.10 | 1.30 | 2.40 | 1.75 | 1.10 | 1.10 | 0.90 | 0.50 | Skin effect .9 × .9 |

Compound used in this group is - α Sulfo Galanyl Chlorin E6
A 0 (zero) or no denotes that parameter was not observed.

| 1 GROUP # | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 106 | 1 | m | 30.2 | 100.0 | iv | 24.0 | satf | r. leg | 200.0 | 300.0 | 665 | 1.40 | 1.40 | 1.80 | 2.20 | 1.50 | 1.00 | 1.70 | 1.40 | 1.30 | Skin effect .25 × 1.25 |
| 106 | 2 | m | 28.4 | 100.0 | iv | 24.0 | satf | r. leg | 200.0 | 300.0 | 665 | 2.10 | 1.50 | 0.90 | 1.50 | 1.40 | 0.95 | 1.30 | 0.80 | 0.30 | Skin effect 1.2 × 1.1 |
| 106 | 3 | m | 26.2 | 100.0 | iv | 24.0 | satf | r. leg | 200.0 | 300.0 | 665 | 1.90 | 1.50 | 0.85 | 2.00 | 1.60 | 1.00 | 1.75 | 1.30 | 0.85 | Skin effect 1.4 × 1.4 |
| 106 | 4 | m | 29.2 | 100.0 | iv | 24.0 | satf | r. leg | 200.0 | 300.0 | 665 | 1.80 | 1.65 | 0.90 | 2.10 | 1.50 | 1.05 | 1.60 | 1.10 | 1.10 | Skin effect 1.4 × 1.3 |
| 106 | 5 | m | 29.9 | 100.0 | iv | 24.0 | satf | r. leg | 200.0 | 300.0 | 665 | 2.10 | 1.50 | 0.95 | 1.55 | 1.35 | 1.05 | 1.70 | 1.60 | 1.20 | Skin effect 1.4 × 1.4 |
| 106 | 6 | m | 28.4 | 100.0 | iv | 24.0 | satf | r. leg | 200.0 | 300.0 | 665 | 2.00 | 1.80 | 0.90 | 1.85 | 1.65 | 0.80 | 1.40 | 1.10 | 0.80 | Skin effect .95 × .6 |
| 106 | 7 | m | 30.1 | 100.0 | iv | 24.0 | satf | r. leg | 200.0 | 300.0 | 665 | 2.20 | 1.80 | 1.10 | 2.25 | 1.75 | 1.30 | 2.00 | 1.40 | 1.10 | Skin effect 1.25 × 1.0 |
| 106 | 8 | m | 29.6 | 100.0 | iv | 24.0 | satf | r. leg | 200.0 | 300.0 | 665 | 2.25 | 2.10 | 1.10 | 2.15 | 1.70 | 1.10 | 1.90 | 1.40 | 1.00 | Skin effect 1.5 × 1.6 |
| 106 | 9 | m | 30.1 | 100.0 | iv | 24.0 | satf | r. leg | 200.0 | 300.0 | 665 | 1.40 | 1.40 | 0.75 | 1.40 | 1.70 | 1.10 | 1.50 | 1.30 | 1.30 | Skin effect 1.4 × .9 |
| 106 | 10 | m | 30.7 | 100.0 | iv | 24.0 | satf | r. leg | 200.0 | 300.0 | 665 | 1.70 | 1.50 | 1.00 | 2.00 | 2.10 | 1.20 | 1.50 | 1.35 | 0.90 | Skin effect 1.2 × 1.1 |
| 106 | | | | | | | | | | | | | | | | | | | | | | Skin effect 1.4 × 1.4 |

Compound used in this group is - Mono-N-Methyl-D-L-Aspartyl Chlorin E6
A 0 (zero) or no denotes that parameter was not observed.

| 1 GROUP # | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 103 | 1 | m | 32.4 | 100.0 | iv | 24.0 | satf | r. leg | 200.0 | 300.0 | 665 | 1.50 | 1.10 | 0.60 | 1.60 | 1.30 | 0.70 | 1.65 | 1.05 | 1.00 | Skin effect .95 × 1.0 |
| 103 | 2 | m | 27.1 | 100.0 | iv | 24.0 | satf | r. leg | 200.0 | 300.0 | 665 | 1.20 | 0.90 | 0.50 | 1.65 | 1.20 | 0.75 | 1.10 | 0.95 | 0.95 | Skin effect 1.2 × .9 |
| 103 | 3 | m | 32.4 | 100.0 | iv | 24.0 | satf | r. leg | 200.0 | 300.0 | 665 | 1.30 | 1.10 | 0.60 | 1.30 | 1.30 | 0.80 | 1.30 | 1.05 | 1.30 | Skin effect 1.1 × 1.2 |
| 103 | 4 | m | 31.0 | 100.0 | iv | 24.0 | satf | r. leg | 200.0 | 300.0 | 665 | 1.50 | 1.10 | 0.65 | 1.80 | 1.40 | 0.90 | 1.40 | 0.95 | 1.10 | Skin effect 1.05 × .85 |
| 103 | 5 | m | 28.7 | 100.0 | iv | 24.0 | satf | r. leg | 200.0 | 300.0 | 665 | 1.50 | 1.30 | 0.60 | 1.50 | 1.00 | 0.80 | 0.70 | 0.90 | 0.80 | Skin effect .95 × .6 |
| 103 | 6 | m | 27.2 | 100.0 | iv | 24.0 | satf | r. leg | 200.0 | 300.0 | 665 | 1.20 | 0.90 | 0.60 | 1.50 | 1.30 | 0.80 | 1.70 | 1.00 | 1.20 | Skin effect 1.3 × .9 |
| 103 | 7 | m | 29.2 | 100.0 | iv | 24.0 | satf | r. leg | 200.0 | 300.0 | 665 | 1.30 | 1.10 | 0.75 | 1.70 | 1.30 | 1.20 | 1.30 | 1.00 | 0.95 | Skin effect 1.0 × 1.2 |
| 103 | 8 | m | 27.2 | 100.0 | iv | 24.0 | satf | r. leg | 200.0 | 300.0 | 665 | 1.60 | 1.20 | 0.70 | 1.50 | 1.40 | 0.90 | 1.20 | 0.85 | 0.80 | Skin effect 1.2 × 1.3 |
| 103 | 9 | m | 28.7 | 100.0 | iv | 24.0 | satf | r. leg | 200.0 | 300.0 | 665 | 1.30 | 1.10 | 0.75 | 1.70 | 1.50 | 0.80 | 2.00 | 1.30 | 0.65 | Skin effect .9 × .9 |
| 103 | 10 | m | 28.5 | 100.0 | iv | 24.0 | satf | r. leg | 200.0 | 300.0 | 665 | 1.50 | 1.30 | 1.00 | 1.50 | 1.30 | 1.00 | 1.40 | 1.05 | 1.15 | Skin effect 1.3 × 1.3 |
| 103 | 11 | m | 29.2 | 100.0 | iv | 24.0 | satf | r. leg | 200.0 | 300.0 | 665 | 1.40 | 1.10 | 0.70 | 1.40 | 1.40 | 1.00 | 1.30 | 1.20 | 1.05 | Skin effect .9 × .9 |

Compound used in this group is - Mono-N-Methyl-D-L-Aspartyl Chlorin E6
A 0 (zero) or no denotes that parameter was not observed.

| 1 GROUP # | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| | 1 | m | 26.3 | 100.0 | iv | 24.0 | satf | r. leg | 200.0 | 300.0 | 665 | 2.00 | 1.40 | 0.75 | 1.60 | 1.40 | 0.95 | 0.00 | 0.00 | 0.00 | No effect |
| | 2 | m | 26.1 | 100.0 | iv | 24.0 | satf | r. leg | 200.0 | 300.0 | 665 | 1.70 | 1.40 | 0.70 | 2.10 | 1.50 | 1.00 | 0.00 | 0.00 | 0.00 | No effect |

-continued

| 1 GROUP | 2 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| | 3 | m | 23.3 | 100.0 | iv | 24.0 | satf | r. leg | 200.0 | 300.0 | 665 | 1.70 | 1.70 | 0.70 | 2.10 | 1.65 | 1.10 | 0.00 | 0.00 | 0.00 | No effect |
| | 4 | m | 24.8 | 100.0 | iv | 24.0 | satf | r. leg | 200.0 | 300.0 | 665 | 1.70 | 1.60 | 0.80 | 1.80 | 1.80 | 0.90 | 0.00 | 0.00 | 0.00 | White spot on skin = 1.5 × 1.7 Died when evans blue was injected |
| | 5 | m | 25.5 | 100.0 | iv | 24.0 | satf | r. leg | 200.0 | 300.0 | 665 | 2.00 | 1.60 | 0.75 | 2.00 | 1.65 | 1.25 | 0.00 | 0.00 | 0.00 | No effect |
| | 6 | m | 27.5 | 100.0 | iv | 24.0 | satf | r. leg | 200.0 | 300.0 | 665 | 2.20 | 1.70 | 0.85 | 2.20 | 1.60 | 1.20 | 0.00 | 0.00 | 0.00 | No effect |
| | 7 | m | 23.5 | 100.0 | iv | 24.0 | satf | r. leg | 200.0 | 300.0 | 665 | 2.20 | 1.70 | 0.85 | 2.30 | 1.80 | 0.90 | 1.9 × 1.3 Small red spot on skin |
| | 8 | m | 25.8 | 100.0 | iv | 24.0 | satf | r. leg | 200.0 | 300.0 | 665 | 1.60 | 1.75 | 0.80 | 2.40 | 1.70 | 1.30 | 0.00 | 0.00 | 0.00 | No effect |
| | 9 | m | 27.2 | 100.0 | iv | 24.0 | satf | r. leg | 0.0 | 0.0 | 0 | 0.00 | 0.00 | 0.00 | 0.00 | 0.00 | 0.00 | 0.00 | 0.00 | 0.00 | Died overnight after injection |

Compound used in this group is - Mono-N-Methyl-L-Glutamyl Chlorin e₆
A 0 (zero) or no denotes that parameter was not observed.

| 1 GROUP | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 107 | 1 | m | 22.5 | 100.0 | iv | 24.0 | satf | r. leg | 200.0 | 300.0 | 665 | 2.50 | 1.90 | 1.20 | 2.30 | 1.90 | 1.20 | 1.15 | 0.70 | 0.70 | Skin effect .9 × .7 |
| 107 | 2 | m | 22.5 | 100.0 | iv | 24.0 | satf | r. leg | 200.0 | 300.0 | 665 | 2.10 | 1.60 | 1.00 | 2.25 | 1.60 | 1.30 | 0.60 | 0.40 | 0.10 | No skin effect |
| 107 | 3 | m | 22.4 | 100.0 | iv | 24.0 | satf | r. leg | 200.0 | 300.0 | 665 | 1.80 | 1.50 | 1.10 | 2.00 | 1.40 | 1.00 | 0.00 | 0.00 | 0.00 | No effect |
| 107 | 4 | m | 23.6 | 100.0 | iv | 24.0 | satf | r. leg | 200.0 | 300.0 | 665 | 2.10 | 1.60 | 0.95 | 1.80 | 1.35 | 1.00 | 0.65 | 0.50 | 0.25 | No skin effect |
| 107 | 5 | m | 22.8 | 100.0 | iv | 24.0 | satf | r. leg | 200.0 | 300.0 | 665 | 2.20 | 1.60 | 1.10 | 2.35 | 1.40 | 1.15 | 0.00 | 0.00 | 0.00 | No effect |
| 107 | 6 | m | 24.7 | 100.0 | iv | 24.0 | satf | r. leg | 200.0 | 300.0 | 665 | 1.60 | 1.30 | 0.90 | 2.50 | 1.40 | 1.25 | 0.00 | 0.00 | 0.00 | No effect |
| 107 | 7 | m | 20.1 | 100.0 | iv | 24.0 | satf | r. leg | 200.0 | 300.0 | 665 | 1.75 | 1.35 | 1.05 | 1.85 | 1.75 | 1.15 | 0.75 | 0.30 | 0.10 | No skin effect |
| 107 | 8 | m | 24.9 | 100.0 | iv | 24.0 | satf | r. leg | 200.0 | 300.0 | 665 | 2.40 | 1.70 | 1.30 | 2.50 | 1.80 | 1.35 | 0.60 | 0.60 | 0.30 | No skin effect |
| 107 | 9 | m | 25.1 | 100.0 | iv | 24.0 | satf | r. leg | 200.0 | 300.0 | 665 | 1.70 | 1.60 | 1.10 | 2.10 | 1.60 | 1.10 | 1.10 | 0.90 | 0.35 | No skin effect |
| 107 | 10 | m | 23.8 | 100.0 | iv | 24.0 | satf | r. leg | 200.0 | 300.0 | 665 | 2.70 | 1.80 | 1.30 | 2.65 | 1.80 | 1.30 | 1.00 | 0.70 | 0.05 | No skin effect |

Compound used in this group is - Iminodipropionic acid Chlorin E6
A 0 (zero) or no denotes that parameter was not observed.

| 1 GROUP | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 104 | 1 | m | 27.0 | 100.0 | iv | 24.0 | satf | r. leg | 200.0 | 300.0 | 665 | 1.90 | 1.30 | 0.80 | 1.80 | 1.35 | 0.90 | 0.70 | 0.75 | 0.20 | Skin effect .95 × .85 |
| 104 | 2 | m | 25.4 | 100.0 | iv | 24.0 | satf | r. leg | 200.0 | 300.0 | 665 | 1.90 | 1.30 | 0.85 | 1.90 | 1.20 | 1.10 | 1.10 | 1.00 | 0.40 | Skin effect 1.3 × 1.0 |
| 104 | 3 | m | 26.3 | 100.0 | iv | 24.0 | satf | r. leg | 200.0 | 300.0 | 665 | 2.20 | 1.50 | 0.90 | 2.00 | 1.40 | 1.10 | 1.50 | 0.70 | 0.60 | Skin effect .65 × .60 |
| 104 | 4 | m | 27.2 | 100.0 | iv | 24.0 | satf | r. leg | 200.0 | 300.0 | 665 | 2.00 | 2.00 | 0.90 | 2.30 | 1.90 | 1.10 | 1.60 | 1.40 | 0.60 | Skin effect .85 × 1.0 |
| 104 | 5 | m | 25.5 | 100.0 | iv | 24.0 | satf | r. leg | 200.0 | 300.0 | 665 | 2.00 | 1.40 | 0.80 | 2.20 | 1.40 | 1.05 | 1.15 | 1.00 | 0.65 | Skin effect .9 × .9 |
| 104 | 6 | m | 27.6 | 100.0 | iv | 24.0 | satf | r. leg | 200.0 | 300.0 | 665 | 2.00 | 2.00 | 1.00 | 2.60 | 2.10 | 1.10 | 1.00 | 1.00 | 0.50 | No skin effect |
| 104 | 7 | m | 27.2 | 100.0 | iv | 24.0 | satf | r. leg | 200.0 | 300.0 | 665 | 2.40 | 1.90 | 0.90 | 2.30 | 1.75 | 1.00 | 0.75 | 0.85 | 0.30 | Skin effect .35 × .35 |
| 104 | 8 | m | 25.4 | 100.0 | iv | 24.0 | satf | r. leg | 200.0 | 300.0 | 665 | 2.20 | 1.70 | 0.95 | 2.30 | 2.00 | 1.00 | 1.15 | 1.20 | 0.60 | No skin effect |
| 104 | 9 | m | 27.2 | 100.0 | iv | 24.0 | satf | r. leg | 200.0 | 300.0 | 665 | 2.50 | 1.60 | 1.10 | 2.70 | 1.90 | 1.20 | 1.10 | 0.90 | 0.60 | Skin effect .9 × .85 |
| 104 | 10 | m | 26.6 | 100.0 | iv | 24.0 | satf | r. leg | 200.0 | 300.0 | 665 | 2.00 | 2.00 | 0.90 | 2.00 | 1.60 | 1.30 | 1.00 | 0.95 | 0.50 | Skin effect .9 × .9 |

Compound used in this group is - Chlorin E6 Iminodiacetic acid
A 0 (zero) or no denotes that parameter was not observed.

| 1 GROUP | 3 MOUSE # | 4 SEX | 5 MOUSE WHT | 6 DOSE | 7 METHOD | 8 TIME | 9 TUMOR TYPE | 10 TUMOR POSIT | 11 LIGHT INTEN | 12 LIGHT DOSE | 13 WAVE LEN | 15 LEN 1 | 16 WID 1 | 17 DEP 1 | 19 LEN 2 | 20 WID 2 | 21 DEP 2 | 22 LEN 3 | 23 WID 3 | 24 DEP 3 | 25 COMMENT |
|---|---|---|---|---|---|---|---|---|---|---|---|---|---|---|---|---|---|---|---|---|---|
| 108 | 1 | m | 25.9 | 100.0 | iv | 24.0 | satf | r. leg | 200.0 | 300.0 | 665 | 2.50 | 1.80 | 1.10 | 2.20 | 1.95 | 1.15 | 0.80 | 0.75 | 0.20 | No skin effect |
| 108 | 2 | m | 23.2 | 100.0 | iv | 24.0 | satf | r. leg | 200.0 | 300.0 | 665 | 2.30 | 1.80 | 1.30 | 2.50 | 1.90 | 1.35 | 0.50 | 0.40 | 0.20 | No skin effect |
| 108 | 3 | m | 24.5 | 100.0 | iv | 24.0 | satf | r. leg | 200.0 | 300.0 | 665 | 2.10 | 1.80 | 1.00 | 2.40 | 1.80 | 1.50 | 0.85 | 0.50 | 1.50 | No skin effect |
| 108 | 4 | m | 24.2 | 100.0 | iv | 24.0 | satf | r. leg | 200.0 | 300.0 | 665 | 2.20 | 1.60 | 1.00 | 2.40 | 1.40 | 1.30 | 0.80 | 0.50 | 0.30 | No skin effect |

-continued

| | | | | | | | | | | | | | | | | | | | | |
|---|---|---|---|---|---|---|---|---|---|---|---|---|---|---|---|---|---|---|---|---|
| 108 | 5 | m | 26.9 | 100.0 | iv | 24.0 | satf | r. leg | 200.0 | 300.0 | 665 | 2.70 | 1.90 | 1.20 | 2.15 | 1.50 | 1.00 | 0.00 | 0.00 | 0.00 | No skin effect |
| 108 | 6 | m | 22.7 | 100.0 | iv | 24.0 | satf | r. leg | 200.0 | 300.0 | 665 | 1.90 | 1.70 | 1.10 | 2.50 | 1.70 | 1.20 | 0.65 | 0.50 | 0.40 | No skin effect |
| 108 | 7 | m | 24.6 | 100.0 | iv | 24.0 | satf | r. leg | 200.0 | 300.0 | 665 | 2.20 | 2.10 | 1.30 | 2.50 | 1.70 | 1.30 | 0.90 | 0.60 | 0.40 | No skin effect |
| 108 | 8 | m | 25.8 | 100.0 | iv | 24.0 | satf | r. leg | 200.0 | 300.0 | 665 | 2.90 | 2.00 | 1.40 | 2.35 | 1.90 | 1.40 | 0.50 | 0.40 | 0.25 | No skin effect |
| 108 | 9 | m | 23.1 | 100.0 | iv | 24.0 | satf | r. leg | 200.0 | 300.0 | 665 | 2.50 | 1.65 | 1.30 | 1.90 | 1.65 | 1.25 | 0.00 | 0.00 | 0.00 | No skin effect |
| 108 | 10 | m | 29.0 | 100.0 | iv | 24.0 | satf | r. leg | 200.0 | 300.0 | 665 | 2.60 | 2.00 | 1.30 | 2.80 | 1.80 | 1.30 | 0.20 | 0.20 | 0.10 | No skin effect |

Compound used in this group is - Mono-N-Methyl-L-Serinyl Chlorin E6
A 0 (zero) or no denotes that parameter was not observed.
1. Animal group number.
3. Mouse number in experiment.
4. Sex of mouse.
5. Weight of mouse in grams.
6. Drug dose mg/kg.
7. Method of drug introduction.
8. Time in hours between drug introduction and light treatment.
9. Tumor type.
10. Position of tumor on animal.
11. Light treatment intensity in mw/cm$^2$.
12. Light dose in J/cm$^2$.
13. Wave length used to treat the tumor in nanometers.
15. Length in cm of tumor on injection date.
16. Width in cm of tumor on injection date.
17. Width in cm of tumor on injection date.
18. Date animal was sacrificed.
19. Length in cm of tumor on date of sacrifice.
20. Width in cm of tumor on date of sacrifice.
21. Depth in cm of tumor on date of sacrifice.
22. Length in cm of effect upon tumor on date of sacrifice.
23. Width in cm of effect upon tumor on date of sacrifice.
24. Depth in cm of effect upon tumor on date of sacrifice.
25. Comments as the result of tumor assessment.

The results of Example 24 are summarized below:

MOUSE TUMOR NECROSIS RESULTS
Tumor Line - SMT-F

| Compound | drug dose mg/kg | method of injection | time in hrs between drug-dose & light | tumor type | light intensity mW/cm² | light length J/cm² | Wavelength nm | (n) | X + s.d. (cm) | range cm |
|---|---|---|---|---|---|---|---|---|---|---|
| Trans-4-Hydroxy-L-Proline Chlorin $e_6$ | 100 | iv | 24 | SMT-F | 200 | 300 | 665 | 10 | 0.230 + .172 | 0.00 − − |
| Mono-N-Methyl-D-L-Aspartyl Chlorin $e_6$ | 100 | iv | 24 | SMT-F | 200 | 300 | 665 | 11 | 1.000 + .193 | 0.65 − − |
| Chlorin $e_6$ Iminodiacetic acid | 100 | iv | 24 | SMT-F | 200 | 300 | 665 | 10 | 0.500 + .150 | 0.20 − − |
| Mono-N-Methyl-Glutamyl Chlorin $e_6$ | 100 | iv | 24 | SMT-F | 200 | 300 | 665 | 7 | 0.000 + .000 | 0.00 − .000 |
| alfa Sulfo β alanyl Chlorin $e_6$ | 100 | iv | 24 | SMT-F | 200 | 300 | 665 | 9 | 1.010 + .291 | 0.30 − 1.30 |
| Iminodipropionic acid Chlorin $e_6$ | 100 | iv | 24 | SMT-F | 200 | 300 | 665 | 10 | 0.185 + .195 | 0.00 − 0.70 |
| Mono-N-Methyl-L-Serinyl Chlorin $e_6$ | 100 | iv | 24 | SMT-F | 200 | 300 | 665 | 10 | 0.220 + .102 | 0.00 − 0.40 | wherein
n is the number of tumors tested.
X is the mean depth of necrosis in cm of the tumor tissue, i.e., the distance from the necrotic top of the tumor next to the skin to the necrotic edge of the tumor most distant from the skin.
S.D. is the standard deviation of X.
range is range of depth of necrosis in cm within the group.

EXAMPLE 25

SCREENING OF PORPHYRIN FLUORESCENCE AS A FUNCTION OF MOLECULAR STRUCTURE

This set of experiments were carried out on DBA/2 Ha Ros-d+Ha mice using the transplantable tumor SmT-F. The tumors were transplanted intramuscularly on the rear of the thigh of the mice. After 10–14 days, when the tumors reached the appropriate size, 2 mg (0.5 ml) of an amino acid porphyrin adduct solution were introduced intraperitoneally into the mice. The amino acid porphyrin adduct solution was prepared as follows: 4 mg of the amino acid porphyrin was dissolved in 0.1M NaOH and adjusted to physiological pH with 1M HCl.

The mice were killed 24 hours after the injection. The tumor was bisected in situ. The porphyrin fluorescence was determined under a constant intensity Uv light source.

Table V lists porphyrin derivatives tested.

Following the name of the porphyrin is a number that indicates the total number of tumors examined. The next column indicates the % of fluorescence. The next column of figures (A) is a number calculated as follows: the porphyrin fluorescence within the tumor was ranked visually by one person under a constant intensity U.V. light source according to the scale 0, +½. 1, 2, 3, 4. This number was then multiplied by the percent of the tumor demonstrating this fluorescence, i.e., (+½) (80%)+(+1) (10%)=50. More often than not, the A valve in the table represent averages obtained in several series of separate experiments conducted at different times.

However, since the amount of fluorescence is dependent upon the size of the tumor, a "C" value was defined in order to compensate for this factor. The "C" value for each tumor is the "A" value for that tumor divided by the average diameter of the tumor, in cm.

MOUSE TUMOR FLUORESCENCE RESULTS
Tumor Line - SMT-F

| Derivatives | # of Tumors | Avg. Diam. of Tumors (cm) | % Fluores. | A | C |
|---|---|---|---|---|---|
| Trans-4-Hydroxy-L-Proline Chlorin $e_6$ | 5 | 1.6 | 17 | 14 | 9 |
| Mono-N-Methyl-D-L-Aspartyl Chlorin $e_6$ | 10 | 2.3 | 48 | 90 | 40 |
| Iminodiacetic acid Chlorin $e_6$ | 5 | 1.6 | 19 | 16 | 10 |
| Mono-N-Methyl-L-Glutamyl Chlorin $e_6$ | 10 | 2.1 | 37 | 65 | 30 |
| Alpha Sulfo β alanyl Chlorin $e_6$ | 5 | 1.8 | 18 | 14 | 8 |
| Iminodipropionic Acid Chlorin $e_6$ | 5 | 1.7 | 17 | 21 | 13 |
| Mono-N-Methyl-L-Serinyl Chlorin $e_6$ | 10 | 1.6 | 21 | 24 | 15 |

*DOSE
100 mg/kg each compound examined 24 hours after intraperitoneal injection

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A fluorescent mono-, di-, tri- or tetramide of amino acid and a carboxy containing tetrapyrrole compound of the formula:

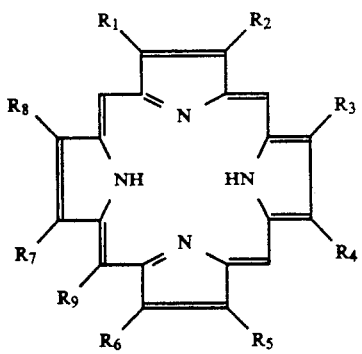

or the corresponding di- or tetrahydrotetrapyrroles, said amide linkage being formed between the amino group of the amino acid and a carboxy-containing substituent attached to the tetrapyrrole; wherein $R_1$ is methyl,

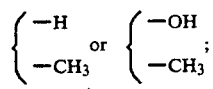

$R_2$ is H, vinyl, ethyl,

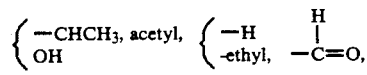

$CH_2CH_2CO_2H$, or =CHCHO;
$R_3$ is methyl,

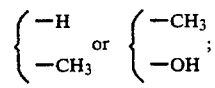

$R_4$ is H, vinyl, ethyl,

CHCH$_3$
OH, $CH_2CH_2CO_2H$, =CHCHO, or

$R_5$ is methyl;
$R_6$ is H, $CH_2CH_2CO_2H$, $CH_2CH_2CO_2R$ or $CO_2H$;
$R_7$ is $CH_2CH_2CO_2H$, $CH_2CH_2CO_2R$ or

$R_8$ is methyl or

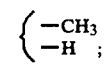

$R_9$ is H, COOH, $CH_2COOH$ or methyl;
provided that when $R_1$, $R_2$, $R_3$, $R_4$, $R_7$ and $R_8$ represent two substituents or are divalent and attached to the same carbon, the respective pyrrole ring to which attached is a dihydropyrrole;

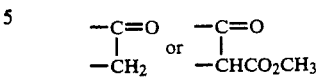

with the proviso that at least one of $R_1$–$R_9$ includes a free carboxyl group; and salts thereof; and wherein the amino acid has the formula:

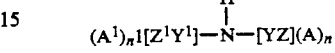

wherein
each $A^1$ and A may be the same or different and are selected from the group consisting of COOH, SO$_3$H or OH with the proviso that said compound contains at least one COOH or SO$_3$H;

$Z^1$ and Z are independently an alkylene chain containing from 0–5 carbon atoms in the principal chain and up to a total of 8 carbon atoms;

$Y^1$ and Y are independently an alkylene chain containing from 0–5 carbon atoms in the principal chain and up to a total of 8 carbon atoms with the proviso that when both A and $A^1$ are other than SO$_3$H, then one of $Y^1$ or Y must contain at least one carbon atom in the principal chain; or $Y^1$ and Y taken together with the nitrogen to which they are attached form an N-heterocycle containing from 4–9 ring carbon atoms and up to a total of about 15 carbon atoms; or $Y^1Z^1$ or YZ individually may form a cycloalkyl group containing from 5 to 10 ring carbon atoms and up to a total of about 16 carbon atoms;

$n^1$ and n are independently 0, 1 or 2; and
$n^1 + n = 2$.

2. The compound according to claim 1 wherein the tetrapyrrole is a porphyrin.

3. The compound according to claim 1 wherein the tetrapyrrole is a bacteriochlorin.

4. The compound according to claim 1 wherein the tetrapyrrole is a chlorin.

5. The compound according to claim 3 wherein the bacteriochlorin is bacteriochlorin $e_4$, bacterioisochlorin $e_4$, bacteriopheophorbide or bacteriochlorin $e_6$.

6. The compound according to claim 2 wherein the porphyrin is mesoporphyrin IX, protoporphyrin IX, deuteroporphyrin IX, coproporphyrin III or hematoporphyrin IX.

7. The compound according to claim 4 wherein the chlorin is transmesochlorin IX, chlorin $e_4$, mesochlorin $e_4$, isochlorin $e_4$, pyropheophorbide a, pheophorbide a or protoporphyrin IX.

8. The compound according to claim 4 wherein the chlorin has the formula:

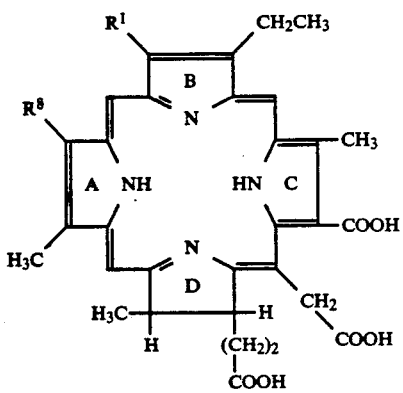

wherein
R¹ is methyl or formyl; and
R⁸ is hydrogen, vinyl, ethyl, acetyl or formyl.

9. The compound according to claim 8 wherein the chlorin is chlorin e₆.

10. The compound according to claim 8 wherein the chlorin is mesochlorin e₆.

11. The compound according to claim 8 wherein the chlorin is 2-desvinyl chlorin e₆.

12. The compound according to claim 8 wherein the chlorin is 2-acetyl chlorin e₆.

13. The compound according to claim 8 wherein the chlorin is 2-formylchlorin e₆.

14. The compound according to claim 8 wherein the chlorin is rhodin g₇.

15. The compound according to claim 1 wherein n¹ is 0 and n is 2.

16. The compound according to claim 1 wherein n¹ is 1 and n is 1.

17. The compound according to claim 1 wherein Z¹Y¹ and YZ each contain 1-3 carbon atoms.

18. The compound according to claim 1 wherein the amino acid has the formula:

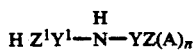

wherein
n¹ is 0;
n is 2;
Z¹Y¹ and YZ are independently an alkylene chain containing from 1-5 carbon atoms; and
each A is independently OH, SO₃H or CO₂H with the proviso that at least one A is SO₃H or CO₂H.

19. The compound according to claim 1 wherein the amino acid has the formula:

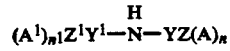

wherein
n¹ is 1;
n is 1;
Z¹Y¹ and YZ are independently an alkylene chain containing from 1-5 carbon atoms and each A and A¹ is independently OH, SO₃H or CO₂H with the proviso that at least one of A and Al is SO₃H or CO₂H.

20. The compound according to claim 1 wherein the amino acid has the formula:

wherein
n¹ is 1;
n is 1;
Y¹ and Y taken together with the nitrogen to which they are attached form a cyclic structure containing from 4–9 ring carbon atoms and a total of from 5–15 carbon atoms;
Z and Z¹ are independently an alkylene chain containing 0–3 carbon atoms; and
A and A¹ are independently OH, CO₂H or SO₃H, with the proviso that at least one of A or A¹ is CO₂H or SO₃H.

21. The compound according to claim 1 wherein the amino acid has the formula:

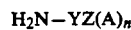

wherein
Y and Z are independently an alkylene chain containing from 1-5 carbon atoms in the principal chain; or
Y and Z taken together form a cycloalkyl compound containing from 5–10 carbon atoms;
each A is OH, SO₃H or COOH with the proviso that at least one A is SO₃H; and
n is 2.

22. The compound according to claim 8 wherein the amino acid has the formula:

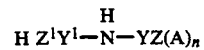

wherein
n¹ is 0;
n is 2;
Z¹Y¹ and YZ are independently an alkylene chain containing from 1-5 carbon atoms; and
each A is independently OH, SO₃H or CO₂H with the proviso that at least one A is SO₃H or CO₂H.

23. The compound according to claim 8 wherein the amino acid has the formula:

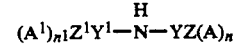

wherein
n¹ is 1;
n is 1; and
Z¹Y¹ and YZ are independently an alkylene chain ng from 1-5 carbon atoms and each A and A¹ is independently OH, SO₃H or CO₂H with the proviso that at least one of A or A¹ is SO₃H or CO₂H.

24. The compound according to claim 8 wherein the amino acid has the formula:

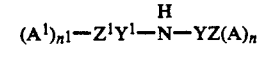

wherein
n¹ is 1;
n is 1;
Y¹ and Y taken together with the nitrogen to which they are attached form a cyclic structure containing from 4-9 ring carbon atoms and a total of from 5-15 carbon atoms;

Z and $Z^1$ are independently an alkylene chain containing 0-3 carbon atoms; and A and $A^1$ are independently OH, $CO_2H$ or $SO_3H$ with the proviso that at least one of A and $A^1$ is $CO_2H$ or $SO_3H$.

25. The compound according to claim 8 wherein the amino acid has the formula:

$$H_2N-YZ(A)_n$$

wherein

Y and Z are independently an alkylene chain containing from 1-5 carbon atoms in the principal chain; or Y and Z taken together form a cycloalkyl compound containing from 5-10 carbon atoms;

each A is OH, $SO_3H$ or COOH with the proviso that at least one A is $SO_3H$; and n is 2.

26. The compound according to claim 1 which is trans-4-hydroxy-L-proline chlorin $e_6$.

27. The compound according to claim 1 which is Mono-N-methyl-DL-Aspartyl chlorin $e_6$.

28. The compound according to claim 1 which is iminodiacetic acid chlorin $e_6$.

29. The compound according to claim 1 which is iminodipropionic acid chlorin $e_6$.

30. The compound according to claim 1 which is mono-N-methyl-L-serinyl chorin $e_6$.

31. The compound according to claim 1 which is α-sulfo-β-alanyl chlorin $e_6$.

32. The compound according to claim 1 which is mono-N-methyl-L-glutamyl chlorin $e_6$.

* * * * *